United States Patent [19]

Hetherington

[11] Patent Number: Plant 6,196

[45] Date of Patent: Jun. 7, 1988

[54] ORCHID-L.C. TRICK OR TREAT C.V. ORANGE MAGIC

[75] Inventor: Ernest E. Hetherington, Arcadia, Calif.

[73] Assignee: Steward Orchids, Carpinteria, Calif.

[21] Appl. No.: 854,325

[22] Filed: Apr. 21, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Howard A. Kenyon

[57] ABSTRACT

A new and distinct variety of orchid, more particularly a Laeliocattleya hybrid plant having flowers of rich orange coloration on erectly carried many flowered sprays. The new variety is distinct from siblings of its grex by its outstanding vigorous plant structure as well as richness of coloring of the flowers. The flowers are of exceptional substance which imparts long lasting quality and are well placed on erect strong stems, superior to all siblings of this population. The flower production is also superior to others of the same line of breeding.

1 Drawing Sheet

DISCOVERY OF THE NEW VARIETY

The orchid of this application was discovered by the undersigned discoverer as an outstanding member of a large sibling population of the hybrid Laeliocattleya-Trick or Treat (Herein abbreviated as Lc. Trick or Treat). Prior to 1973 Lc. Trick or Treat had been developed in the orchid nursery of Fred A. Stewart, Inc. at San Gabriel, Calif. by crossing Lc. Icarus, clone #3470 by Lc. Chit Chat 'Tangerine'. The Chit Chat was the pollen parent. The resultant grex of Lc. Trick or Treat was registered by the Stewart nursery with the Orchid Hybrid Registration Committee in Londond, England, and published in 1973 (in Sanders). The new orchid was registered as "Stewart cross #1716 Lc. Trick or Treat".

In February 1977, the new variety appeared as a single outstanding plant among a large population of siblings of Lc. Trick or Treat, all cultivated and blooming at Stewart's San Gabriel nursery. The plant of the new variety was immediately recognizable as superior in its flowering to all other members of the large population of the hybrid group Lc. Trick or Treat. After the new variety had been observed for a period of time, its other features of superior growth and structure were also noted.

ASEXUAL REPRODUCTION

After its discovery in February 1977, the original plant was placed in the laboratories of the Fred A. Stewart Inc. Nursery. During the years since 1977, a large number of plants of the new cultivar have been asexually produced by the meristem tissue method. Portions of tissue called meristem, comprised of unspecialized cells, capable of later differentiation, were cut from the plant, and developed, under carefully controlled sterile conditions into new individual plants. This has been an ongoing process to cultivate this exceptional variety. The population thus produced is carried under the Code Number SM-398. All asexually propagated tissue from this cultivar carries this code number.

All of the propagations reproduced true to the original in both plant, flower and other characteristics. A substantial cross section have flowered. They are exactly the same as the mother clone, with no signs of mutation. All plants of the new variety have continued to be readily distinguishable from both parents and all other siblings of the Lc. Trick or Treat hybrid population. The new variety has been designated Lc. Trick or Treat 'Orange Magic'.

DESCRIPTION OF THE PHOTOGRAPHS

The lower photograph is a close-up view of a group of flowers typical of the new variety.

The upper photograph shows the same flowers but as viewed from a greater distance, so as to reveal the appearance of the plant foliage and flowers.

DESCRIPTION OF THE PLANT

The plant and its flowers are illustrated in the color photographs accompanying this specification. In some respects, the plant is typical of bifoliate cattleya hybrid orchids. Its strap-like leaves are coriacious bifoliate, which is characteristic of this grex and its cultivar 'Orange Magic'. The average leaf is 22.5 centimeters to 30.0 centimeters long. The plant attains a growth on maturity of 37.5 centimeters to 45 centimeters. However, the plant develops a structure of superior and unusual strength and resiliency in all of its parts. The rhizome is short, branching often into a compact plant with many flowering leads. The growth, in addition to being compact, is naturally erect without any need to support the leaves and flower stems. The strong flower sprays are borne in the axils of the bifoliate growths and are of superior strength. Its flowering habit is dependable. The flowers develop from sheaths throughout the winter and spring season. The plants are hardy in comparison with similar orchids. They have been virus and pathogen free during development, both in the original population of Lc. Trick or Treat, in the cultivar 'Orange Magic', and in the meristem population of the new variety, 'Orange Magic'. The cells have an even chromosome complement, which has been proven by successful and frequent use as a parent. There are no characteristics of aneuploidy or aberrant growth habit.

DESCRIPTION OF THE FLOWER

The outstanding merit of the new variety is the richness of coloring of the flowers. Such coloring is difficult to obtain in the degree of intensity in orange flowered Laeliocattleya hybrids. It is even more difficult to obtain strength of stem of the flower spray, number of flowers to the spray, and the carriage of so many flowers on an erect stem.

Both sepals and petals are a rich orange, best identified by The British Horticultural Colour Vol. I, Chart Page 12, Swatch 12. (Close horticultura well known examples are B.H.C.C. *Dimorphotheca aurantiaca* and *Tritonia crocata*.) The texture of sepals and petals is sparkling and clear. The flowers hold their color very well in comparison to others in this line of breeding. The attractive labellum is in nice balance to the sepals and petals and basically the same coloration. The orange side lobes are closed over the column. Within the throat of the labellum, there is a slight amount of light yellow B.H.C.C. Pg. 5, Swatch 5/1. The shading is very subtle, however.

The flowers of the new variety are larger and stronger in structure than the average grex or cultivar in this line of breeding. The flowers average 1.25 cm. in petal width with a total span of 7.5 cm. The new variety can carry as many as 15 flowers on each spray on a mature well grown plant. The flowers are perfectly carried on strong erect flower spikes. The petals are flat and well carried in contrast to other cultivars of this grex and line of breeding. They are carried without twisting, turning, or recurving. The sepals and petals are in symmetrical balance to the lip and create a good round shape to the flower as a whole. The flowers last as long as three to four weeks on the spray.

The blooming season is primarily throughout midwinter into early spring. It can vary according to cultural conditions where it is grown.

The above described characteristics of the new variety make it of superior value in the commercial orchid plant sales market. The exceptional vigor of this particular cultivar, excellent blooming season, total reliability of bloom and freedom of bloom are characteristics which set this particular cultivar above not only its siblings in the grex, but other gregi in this entire line of breeding.

What is claimed is:

1. A new and distinct variety of orchid of the hybrid genus Laeliocattleya, discovered as a superior variety of the grex Lc. Trick or Treat, in particular the cultivar 'Orange Magic', and characterized by a combination of brilliant flower color, superior flower substance, size, and shape, further characterized by its exceptional vigor, reliability of bloom and floriferousness.

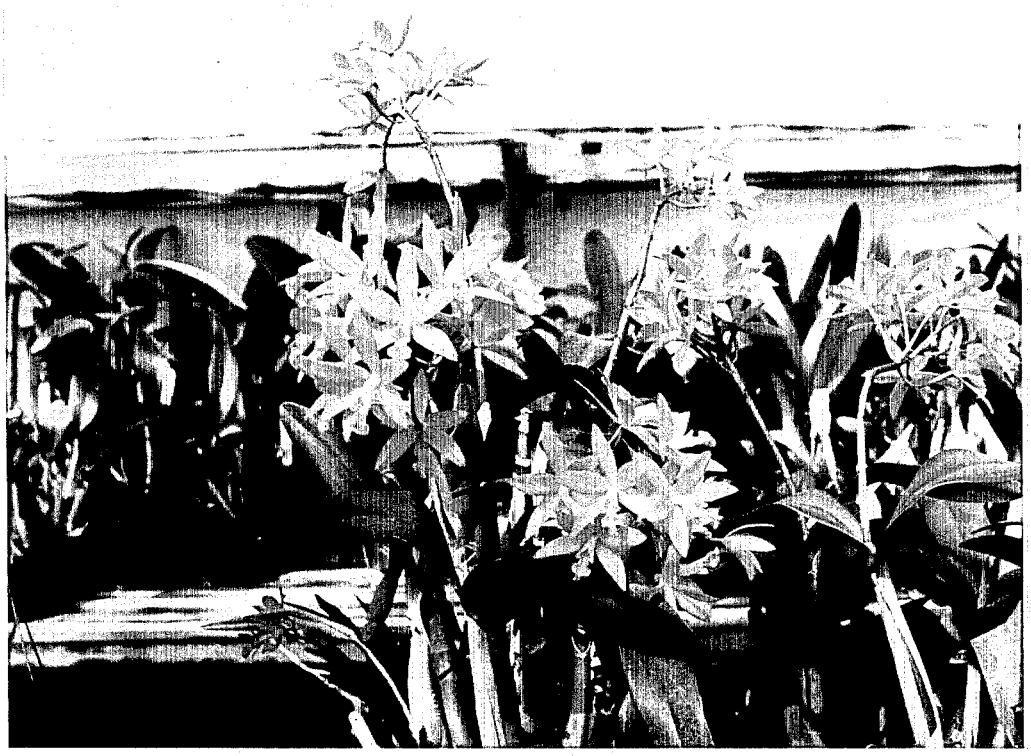
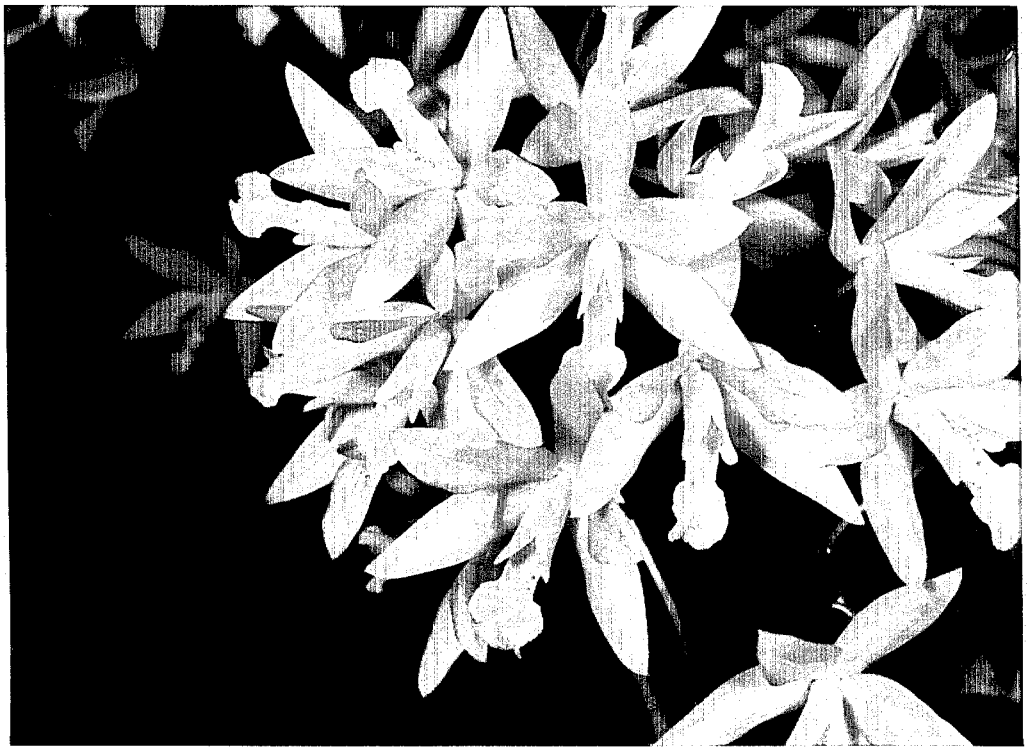

* * * * *